(12) United States Patent
Yen et al.

(10) Patent No.: US 8,498,696 B2
(45) Date of Patent: Jul. 30, 2013

(54) HEALTH MONITORING DEVICE AND HUMAN ELECTRIC SIGNAL PROCESSING METHOD

(75) Inventors: Jia-Yush Yen, Taipei (TW); Fan-Che Yen, Taipei (TW); Chih-Kung Lee, Taipei (TW); Chii-Wann Lin, Taipei (TW); Kuang-Chong Wu, Taipei (TW); Ching-En Tseng, Taipei (TW)

(73) Assignee: National Taiwan University, Taipei (TW)

( * ) Notice: Subject to any disclaimer, the term of this patent is extended or adjusted under 35 U.S.C. 154(b) by 552 days.

(21) Appl. No.: 12/796,634

(22) Filed: Jun. 8, 2010

(65) Prior Publication Data

US 2010/0317934 A1     Dec. 16, 2010

(30) Foreign Application Priority Data

Jun. 15, 2009   (TW) ............................... 98119888 A

(51) Int. Cl.
*A61B 5/04* (2006.01)
(52) U.S. Cl.
USPC ........................................................ 600/509

(58) Field of Classification Search
USPC .................................................. 600/508, 509
See application file for complete search history.

(56) References Cited

U.S. PATENT DOCUMENTS

| | | | | |
|---|---|---|---|---|
| 7,751,873 | B2 * | 7/2010 | de Voir | 600/509 |
| 7,809,433 | B2 * | 10/2010 | Keenan | 600/544 |

FOREIGN PATENT DOCUMENTS

TW             200822904             6/2008

\* cited by examiner

*Primary Examiner* — Christopher D Koharski
*Assistant Examiner* — Frances Oropeza

(57) ABSTRACT

A health monitoring device is provided and includes a detecting unit for detecting a first electric signal from a human body and a processing unit for performing the following steps: receiving the first electric signal; performing wavelet transform on the first electric signal, to filter frequency bands thereof which include undesired noises, and then perform a reverse wavelet transform to obtain a second electric signal; combining frequency bands of the first electric signal which include primary characteristics and then perform a reverse wavelet transform on the combined frequency bands to obtain a fourth electric signal; and comparing the fourth electric signal with a plurality of electric signal patterns of a database to determine whether the fourth electric signal is an electric signal for healthiness.

20 Claims, 4 Drawing Sheets

HEALTH MONITORING DEVICE AND HUMAN ELECTRIC SIGNAL PROCESSING METHOD

CROSS REFERENCE TO RELATED APPLICATIONS

This non-provisional application claims priority under 35 U.S.C. §119(a) on Patent Application No. 098119888, filed in Taiwan, Republic of China on Jun. 15, 2009, the entire contents of which are hereby incorporated by reference.

BACKGROUND OF THE INVENTION

1. Field of the Invention

The present invention relates to health monitoring devices and human electric signal processing methods, and in particular relates to health monitoring devices and human electric signal processing methods using wavelet transform and spectral estimation.

2. Description of the Related Art

In electrocardiograms (ECG), every heart beat period includes a P wave, a Q wave, a R wave, a S wave, a T wave and a U wave. Additionally, every wave has individual physiological representations. Therefore, whether a human being is healthy may be determined by the characteristics of the waves.

For example, the Republic of Chinese Patent (application No. 200822904) discloses a method for locating desired points within an electrocardiogram signal. The method applies wavelet transform and multi-scale differential operations to locate at least a desired point in at least a frequency band within the electrocardiogram signal for health determination. Additionally, after the wavelet transform is performed, coefficients thereof are further used in the multi-scale differential operation.

When people pay more and more attention to their health, utilizing electrocardiogram or other human physical signals to check one's health has become an important issue.

BRIEF SUMMARY OF THE INVENTION

The present invention provides a health monitoring device, which comprises a detecting unit and a processing unit. The detecting unit, detects a first electric signal from a human body; and the processing unit performs the following steps of: receiving the first electric signal; performing wavelet transform on the first electric signal, to filter frequency bands thereof which include undesired noises, and then perform reverse wavelet transform to obtain a second electric signal; combining frequency bands of the first electric signal which include primary characteristics and then perform reverse wavelet transform on the combined frequency bands to obtain a third electric signal; obtaining period information of the second electric signal from the third electric signal, and then re-sampling the second electric signal according to the period information to obtain a fourth electric signal; and comparing the fourth electric signal with a plurality of electric signal patterns in a database to determine whether the fourth electric signal is an electric signal for healthiness.

The present invention also provides a human electric signal processing method, which comprises: receiving a first electric signal of a human body; performing wavelet transform on the first electric signal to filter frequency bands thereof which include undesired noises, and then perform reverse wavelet transform to obtain a second electric signal; combining frequency bands of the first electric signal which include primary characteristics and then performing reverse wavelet transform on the combined frequency bands to obtain a third electric signal; obtaining period information of the second electric signal from the third electric signal, and then re-sampling the second electric signal according to the period information to obtain a fourth electric signal.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
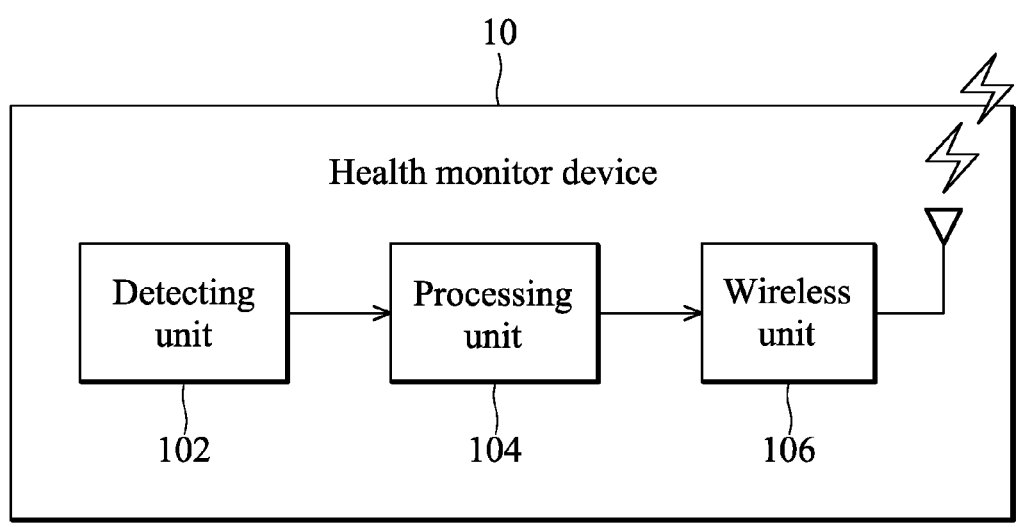
FIG. 1 is a block diagram of a health monitor device according to the present invention.

Please refer to FIG. 1. FIG. 1 is a block diagram of a health monitor device 10 according to the present invention. The health monitor device 10 is disposed on a human body part and detect the health signal of a human body. The health monitor device 10 may be designed to have a watch-like shape to be worn on a patient's wrist, but the invention is not limited thereto. The health monitor device 10 comprises a detecting unit 102, a processing unit 104 and a wireless unit 106.

Figure 2:
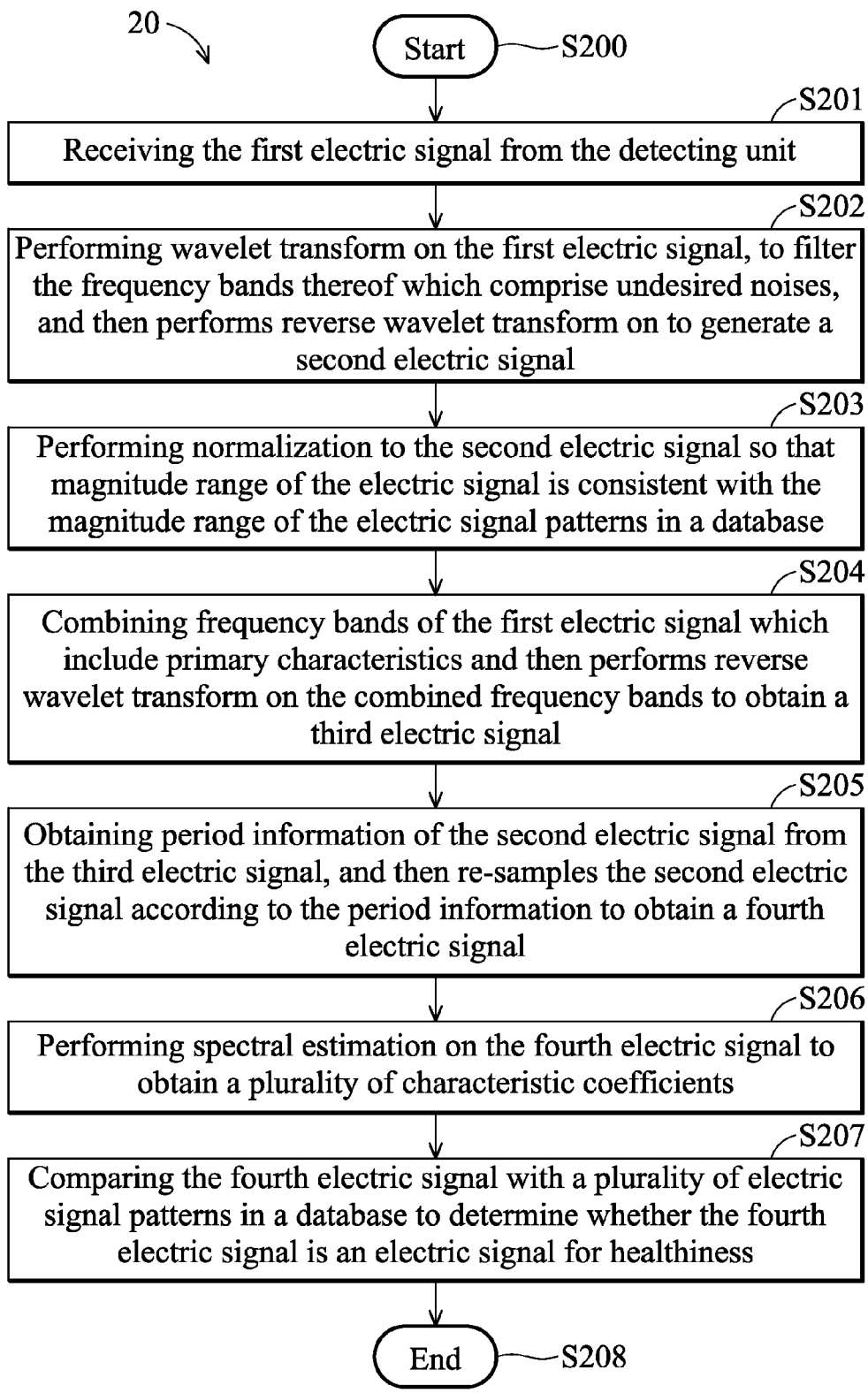
FIG. 2 is a flow chart of a human electric signal processing method performed by the processing unit of FIG. 1.

The detecting unit 102 detects a first electric signal of a human body, and sends the first electric signal to the processing unit 104. In the present invention, the first electric signal may be an electrocardiogram signal. The processing unit 104 is coupled to the detecting unit 102, and receives the first electric signal, determines whether the first electric signal is an electric signal for healthiness, by performing a human electric signal processing method 20 (as shown in FIG. 2), and then sends the result from the determination to the wireless unit 106. After the wireless unit 106 receives the result from the processing unit 104, the result is sent by wireless communications to an external source. For example, the determination result may be sent to a remote health control center, and when the result indicates that the patient under observation is not healthy, the remote health control center would assign medical professionals to help the patient. Note that various communication methods may be used in the wireless unit 106, such as a Wi-Fi, WLAN and WiMAX communication method and others.

Please refer to FIG. 2. FIG. 2 is a flow chart of a human electric signal processing method 20 performed by the processing unit 104 of FIG. 1.

The process starts from step S200.

In step S201, the processing unit 104 receives the first electric signal (electrocardiogram signal) from the detecting unit 102.

Figure 3:
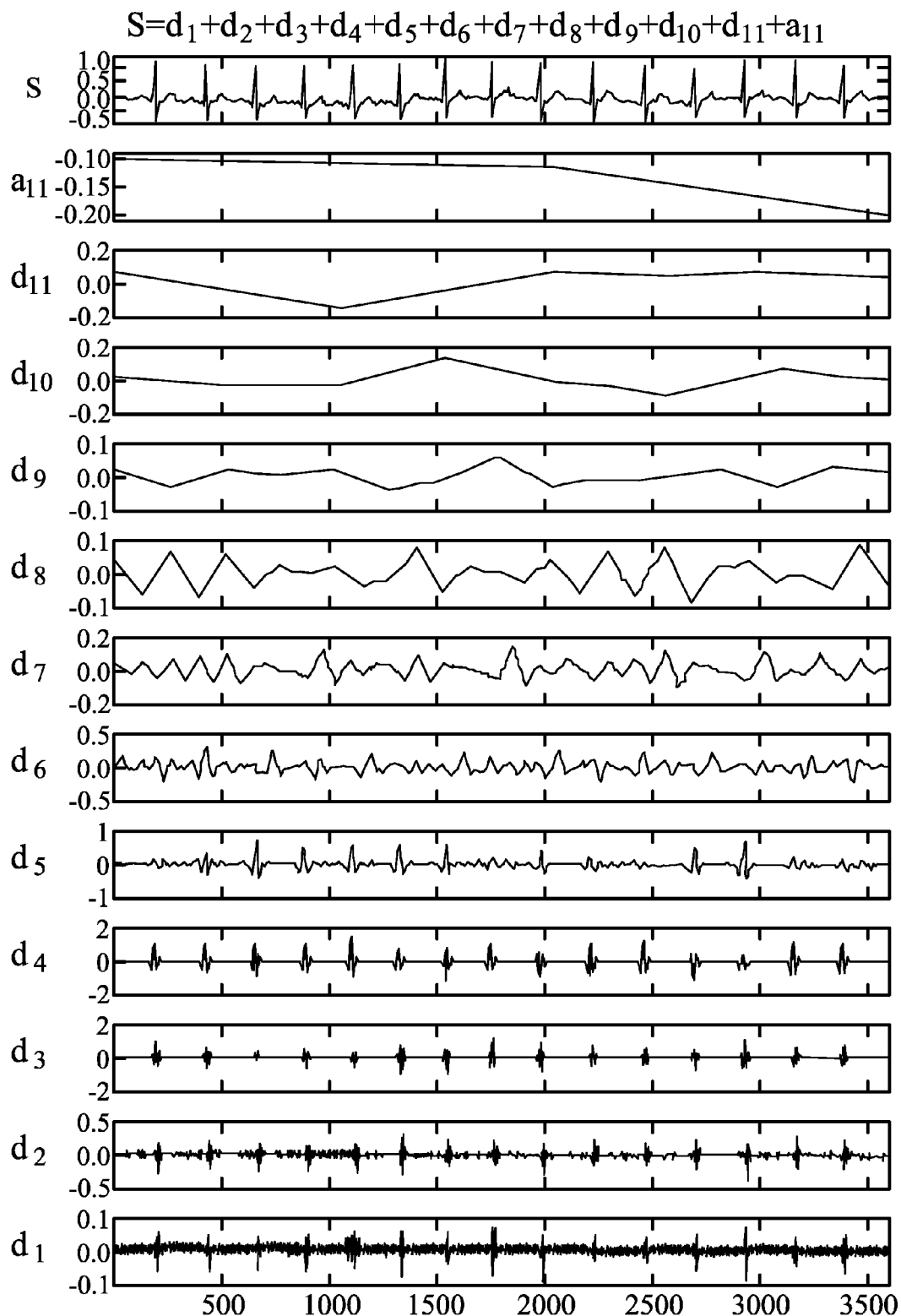
FIG. 3 is a schematic diagram illustrating a plurality of decomposed waveforms after performing a wavelet transform.

In step S202, the processing unit 104 performs wavelet transform on the first electric signal, to filter the frequency bands thereof which comprise undesired noises, and then performs reverse wavelet transform on to generate a second electric signal. The frequency bands which include undesired noises in the first electric signal are low frequency drift bands and high frequency noise bands. For example, refer to FIG. 3, FIG. 3 is a schematic diagram illustrating a plurality of decomposed waveforms after performing a db3-based wavelet transform. The wavelet transform technique is well-known in the prior art and will not be discussed hereinafter. In FIG. 3, the signal S is the first electric signal, and after 11 levels of wavelet transform, the signals $d_1, d_2, d_3, d_4, d_5, d_6, d_7, d_8, d_9, d_{10}, d_{11}$ and $a_{11}$ are generated. Note that $S=d_1+d_2+d_3+d_4+d_5+d_6+d_7+d_8+d_9+d_{10}+d_{11}+a_{11}$, wherein the signals $d_1$ and $d_2$ belong to high frequency noise bands, and the signals $d_9, d_{10}, d_{11}$ belong to low frequency drift bands. Therefore, in step S202, the signals may be eliminated and the de-noised second electric signal will be constructed after the wavelet transform is completed.

In step S203, the processing unit 104 performs normalization to the second electric signal so that magnitude range of the electric signal is consistent with the magnitude range of the electric signal patterns in a database. For an electrocardiogram diagnosis, the waveform, the wavelength, and the amplitude of the electric signal patterns are all important parameters to be estimated, thus, all of the signals in the database would be adjusted to be within the same scale for comparison. Therefore, in step S203, the magnitude of the second electric signal may be normalized so that the magnitude range of the electric signal is consistent with the magnitude range of the electric signal patterns in the database. For example, when the voltages of the electric signal patterns in the database are within −1~+1 mV, the voltage of the second electric signal would be normalized to be within the rage (−1~+1 mV).

Figure 4A:
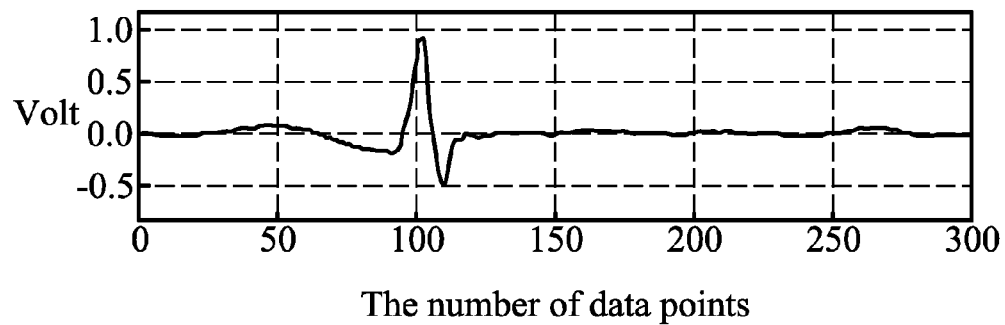
FIG. 4a is a schematic diagram of a QRS waveband after combining the signals d3 and d4 and then performing a reverse wavelet transform on the combined signals.
Figure 4B:
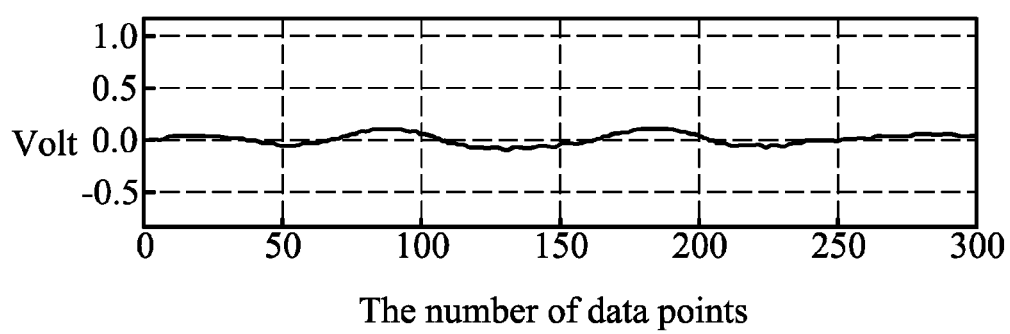
FIG. 4b is a schematic diagram of a P, T, and U waveband after combining the signals d6, d7 and d8 and then performing a reverse wavelet transform on the combined signals.

In step S204, the processing unit 104 combines frequency bands of the first electric signal which include primary characteristics and then performs reverse wavelet transform on the combined frequency bands to obtain a third electric signal. The frequency bands which include primary characteristics further comprise a QRS waveband, a P waveband, a T waveband, and a U waveband. For example, referring to FIG. 3, the primary characteristics of a QRS waveband are located in the signals $d_3$ and $d_4$, and the primary characteristics of the P, T and U wavebands are located in the signals $d_6$, $d_7$ and $d_8$. Therefore, by combining the signals $d_3$ and $d_4$, and combining the signals $d_6$, $d_7$ and $d_8$, and then performing a reverse wavelet transform on the combined frequency bands, a main desired signal in the electrocardiogram may be obtained. FIG. 4a shows a QRS waveband after combining the signals $d_3$ and $d_4$ and then performing a reverse wavelet transform on the combined signals; and FIG. 4b shows a P, T, and U waveband after combining the signals $d_6$, $d_7$ and $d_8$ and then performing a reverse wavelet transform on the combined signals.

In step S205, the processing unit 104 obtains period information of the second electric signal from the third electric signal, and then re-samples the second electric signal according to the period information to obtain a fourth electric signal. Note that the processing unit 104 utilizes the QRS waveband or the P, T, and U wavebands obtained from step S204, to obtain a heart beat period, and then obtains the second electric signal which has a single period according to the heart beat period Then, the processing unit 104 re-samples the second electric signal with the single period to obtain a fourth electric signal. Everyone has his own heart beat period, and the number of data points in a single heart beat period are usually different from one to one, which causes the characteristics in frequency domain unable to be compared with the other ones under the same standards, thus, a step for re-sampling the data points is necessary, In this embodiment, the number of re-sampled data points is 300, but the number is not limited thereto in other embodiments.

In step S206, the processing unit 104 performs spectral estimation on the fourth electric signal to obtain a plurality of characteristic coefficients. For example, spectral estimation is performed by using Autoregressive Model (AR Model) to obtain the characteristic coefficients, and the characteristic coefficients may be three coefficients of a 3-order ARM. The ARM may forecast the following output according to the previous outputs, and the 3-order ARM relationship is shown below:

$$y[n]=a1*y[n-1]+a2*y[n-2]+a3*y[n-3]+u[n] \quad (A)$$

wherein y[n] is the fourth electric signal, y[n−1], y[n−2], y[n−3] are electric signals previously measured, u[n] is noise, and a1, a2 and a3 are correlation coefficients. The characteristic coefficients obtained in step S206 are the correlation coefficients described above. In this embodiment, the 3-order ARM is taken as an example, but those skilled in the art may use other ARMs with higher orders (5-order, 6-order, etc.) to obtain more characteristic coefficients in other embodiments.

In step S207, the processing unit 104 compares the fourth electric signal with a plurality of electric signal patterns in a database to determine whether the fourth electric signal is an electric signal for healthiness. Step S207 may be performed by a Support Vector Machine (SVM). First, the processing unit 104 may couple the fourth electric signal to the characteristic coefficients (a1, a2, and a3) in series to generate a new characteristic $\vec{x}$; and then, output the new characteristic $\vec{x}$ to the SVM. The SVM is performed by the x following equation (B):

$$f(x) = \text{sgn}\left(\sum_{i=1}^{N} \alpha_i^* y_i \exp\left(-\frac{1}{\sigma^2}\|\vec{x}-\vec{x}_j\|^2\right) + b\right) \quad (B)$$

wherein $\alpha_i^*$ is Lagrange multipliers; $\vec{x}_j$ is generated by coupling the electric signal patterns in the database to their corresponding characteristic coefficients in series; and $y_i$ indicates that $\vec{x}_j$ is health patterns or ill health patterns. For example, when $\vec{x}_j$ is a pattern for health, $y_i$ is smaller than zero; otherwise, $y_i$ is greater than zero. Moreover, $$\exp\left(-\frac{1}{\sigma^2}\|\vec{x}_i-\vec{x}_j\|^2\right)$$

is a Radial-basis function (RBF) Kernel function, and the SVM is performed by using RBF Kernel function to map data to a high dimension space to improve accuracy for data comparison. Meanwhile, b is a correlation value. By using the function (B), the SVM may compare the new characteristic $\vec{x}$ with the numerous patterns $\vec{x}_j$ in the database. When the result of the equation (B) is greater than zero, the fourth electric signal may be determined as a signal for ill health; otherwise, when the result of the equation (B) is smaller than zero, the fourth electric signal may be determined as a signal for healthiness.

In step S208, the steps end.

In summary, the present invention firstly performs the wavelet transform technique to the electrocardiogram to eliminate undesired noises, normalizes and re-samples. Secondly, spectral estimation is performed to obtain characteristic coefficients and the characteristic coefficients are coupled to the processed electrocardiogram signal in series to generate new characteristics. Finally, the present invention compares the new characteristics by utilizing SVM to determine whether the fourth electric signal is an electric signal for healthiness.

Note that the present invention is not limited to application only to an electrocardiogram signal. Other electric signals such as electroencephalogram signals, electromyogram signals or blood sugar level concentration signals may also be applied. Moreover, in the embodiment discussed above, while normalization is performed to the second electric signal, however, the normalization may also be performed to the first electric signal in step S201 or to the fourth electric signal in step S205.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A health monitoring device, comprising:
   a detecting unit for detecting a first electric signal from a human body; and
   a processing unit for performing the following steps:
      receiving the first electric signal;
      performing wavelet transform on the first electric signal, to filter frequency bands thereof which include undesired noises, and then perform reverse wavelet transform to obtain a second electric signal;
      combining frequency bands of the first electric signal which include desired primary characteristics and then performing reverse wavelet transform on the combined frequency bands to obtain a third electric signal;
      obtaining period information of the second electric signal from the third electric signal, and then re-sampling the second electric signal according to the period information to obtain a fourth electric signal; and
      comparing the fourth electric signal with a plurality of electric signal patterns in a database to determine whether the fourth electric signal is an electric signal for healthiness.

2. The health monitoring device as claimed in claim 1, wherein the processing unit further performs the following steps:
   performing spectral estimation on the fourth electric signal to obtain a plurality of characteristic coefficients;
   comparing the characteristic coefficients with a plurality of characteristic coefficient patterns to determine whether the fourth electric signal is an electric signal for healthiness.

3. The health monitoring device as claimed in claim 1, wherein the processing unit further performs the following steps:
   performing normalization on one of the first, second and fourth electric signals so that the magnitude range of the electric signal is consistent with the magnitude range of the electric signal patterns in the database.

4. The health monitoring device as claimed in claim 1, wherein the frequency bands which include undesired noises in the first electric signal are low frequency drift bands and high frequency noise bands.

5. The health monitoring device as claimed in claim 1, wherein the frequency bands of the second bands which include primary characteristics comprise one of a QRS band, P band, T band, or U band.

6. The health monitoring device as claimed in claim 1, wherein the first electric signal is one of an electrocardiogram signal, an electroencephalogram signal, an electromyogram signal or a blood sugar concentration signal.

7. The health monitoring device as claimed in claim 2, wherein spectral estimation is performed by using Autoregressive Model (AR Model).

8. The health monitoring device as claimed in claim 2, wherein step of comparing the fourth electric signal with a plurality of electric signal patterns in a database and step of comparing the characteristic coefficients with a plurality of characteristic coefficient patterns are performed by a Support Vector Machine (SVM).

9. The health monitoring device as claimed in claim 8, wherein the SVM is performed by using a mapping function to map information to a high dimension space, and the mapping function is a Radial-basis function (RBF) Kernel function.

10. The health monitoring device as claimed in claim 1, further comprising a wireless unit, wherein the wireless unit is coupled to the processing unit and transmits the processing unit result by wireless communications, determining whether the fourth electric signal is an electric signal for healthiness.

11. A human electric signal processing method, comprising:
   receiving a first electric signal of a human body;
   performing wavelet transform on the first electric signal, to filter frequency bands thereof which include undesired noises, and then perform reverse wavelet transform to obtain a second electric signal;
   combining frequency bands of the first electric signal which include primary characteristics and then performing reverse wavelet transform on the combined frequency bands to obtain a third electric signal;
   obtaining period information of the second electric signal from the third electric signal, and then re-sampling the second electric signal according to the period information to obtain a fourth electric signal.

12. The human electric signal processing method as claimed in claim 11, further comprising:
   performing spectral estimation on the fourth electric signal to obtain a plurality of characteristic coefficients.

13. The human electric signal processing method as claimed in claim 12, further comprising:
   comparing the fourth electric signal with a plurality of electric signal patterns in a database to determine whether the fourth electric signal is an electric signal for healthiness.

14. The human electric signal processing method as claimed in claim 13, further comprising:
   performing normalization on one of the first, second and fourth electric signals so that the magnitude range of the electric signal is consistent with the magnitude range of the electric signal patterns in the database.

15. The human electric signal processing method as claimed in claim 11, wherein the frequency bands which include undesired noises in the first electric signal are low frequency drift bands and high frequency noise bands.

16. The human electric signal processing method as claimed in claim 11, wherein the frequency bands of the second bands which include primary characteristics comprises one of a QRS band, P band, T band, or U band.

17. The human electric signal processing method as claimed in claim 11, wherein the first electric signal is one of an electrocardiogram signal, an electroencephalogram signal, an electromyogram signal or a blood sugar concentration signal.

18. The human electric signal processing method as claimed in claim 12, wherein spectral estimation is performed by using Autoregressive Model (AR Model).

19. The human electric signal processing method as claimed in claim 13, wherein step of comparing the fourth electric signal with a plurality of electric signal patterns in a database and step of comparing the characteristic coefficients with a plurality of characteristic coefficient patterns are performed by a Support Vector Machine (SVM).

20. The human electric signal processing method as claimed in claim 19, wherein the SVM performs a mapping function to map information to a high dimension space, and the mapping function is a Radial-basis function (RBF) Kernel function.

* * * * *